(12) United States Patent
Shih et al.

(10) Patent No.: US 9,844,543 B2
(45) Date of Patent: Dec. 19, 2017

(54) METHOD OF TREATING OR PREVENTING HYPERLIPIDEMIA WITH CAFFEAMIDE DERIVATIVES

(71) Applicant: Chun-Ching Shih, Taichung (TW)

(72) Inventors: Chun-Ching Shih, Taichung (TW); Yueh-Hsiung Kuo, Taipei (TW); Cheng-Hsiu Lin, Taichung (TW)

(73) Assignee: Chun-Ching Shih, Taichung (TW)

( * ) Notice: Subject to any disclaimer, the term of this patent is extended or adjusted under 35 U.S.C. 154(b) by 0 days.

(21) Appl. No.: 14/800,206

(22) Filed: Jul. 15, 2015

(65) Prior Publication Data

US 2017/0014400 A1    Jan. 19, 2017

(51) Int. Cl.
*A61K 31/4453* (2006.01)
*A61K 31/165* (2006.01)
*A61K 31/40* (2006.01)

(52) U.S. Cl.
CPC ........ *A61K 31/4453* (2013.01); *A61K 31/165* (2013.01); *A61K 31/40* (2013.01)

(58) Field of Classification Search
CPC ... A61K 31/4453; A61K 31/165; A61K 31/40
See application file for complete search history.

(56) References Cited

PUBLICATIONS

Weng et al. 2012 (European Journal of Pharmacology, 684 (2012) 108-115).*
Weng et al. 2010 ( J. Agricultural and food chemistry, 2010, 58 pages 10033-10038).*
Zang et al ((Diabetes, vol. 55, 2006, pp. 2180-2191).*
Yueh-Hsiung Kuo et al., "Caffeamide 36-13 Regulates the Antidiabetic and Hypolipidemic Signs of High-Fat-Fed Mice on Glucose Transporter 4, AMPK Phosphorylation, and Regulated Hepatic Glucose Production", Hindawi Publishing Corporation, Evidence-Based Complementary and Alternative Medicine, vol. 2014, Article ID 821569, 12 pages.

* cited by examiner

*Primary Examiner* — Savitha Rao
(74) *Attorney, Agent, or Firm* — Wang Law Firm, Inc.

(57) ABSTRACT

The present invention provides a method of treating or preventing hyperlipidemia in a subject in need thereof. Such method includes, specifically, administrating to the subject a therapeutically effective amount of a caffeamide derivative. The present invention also provides a pharmaceutical composition containing, primarily, the caffeamide derivative. The method and pharmaceutical composition of the present invention can effectively and significantly lower the high-fat diet-induced body weight gain and absolute visceral fat weight as well as the concentration of triglycerides and free fatty acids in blood, and levels of total lipid and triacylglycerol in liver tissue. In addition, the caffeamide of the present invention also reduces size of adipocyte, hepatocellular ballooning phenomenon, and liver steatosis. Through promotion of phosphorylation of 5' adenosine monophosphate-activated protein kinase (AMPK) in muscle and liver, the caffeamide derivatives of the present invention is suitable for ameliorating or remedying hyperlipidemia.

11 Claims, 7 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
tggaaagata actgggtgac                                                  20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tgctgtcgtc tgtagtcttg                                                  20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
cagttttatc cctagaagca                                                  20

<210> SEQ ID NO 4
<211> LENGTH: 19
<212> TYPE: DNA
<213> ORGANISM: Artificial Sequence
<220> FEATURE:
<223> OTHER INFORMATION: PCR primer

<400> SEQUENCE: 4
tctcacgact caatagctg                                                   19

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
tcttctacaa ccaacagaat ca                                               22

<210> SEQ ID NO 6
<211> LENGTH: 22
<212> TYPE: DNA
<213> ORGANISM: Artificial Sequence
```

```
<220> FEATURE:
<223> OTHER INFORMATION: PCR primer

<400> SEQUENCE: 6
gtatcatggt agagaaggaa gc                                        22

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
tgtgtccgtc gtggatctga                                           20

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
cctgcttcac caccttcttg a                                         21
```

METHOD OF TREATING OR PREVENTING HYPERLIPIDEMIA WITH CAFFEAMIDE DERIVATIVES

BACKGROUND OF THE INVENTION

1. Field of the Invention

The present invention is related to a method of treating or preventing hyperlipidemia. Particularly, the present invention is related to a method of treating or preventing hyperlipidemia with caffeamide derivatives.

2. The Prior Arts

Diabetes mellitus (DM) is a metabolic disease and chronic diabetes mellitus is tightly associated with various metabolic syndromes such as obesity and coronary artery disease. Researches had shown that genetics and environmental factors including obese lifestyle have large influences over type 2 diabetes mellitus (T2D), while experimentations with C57BL/6J mice had indicated that high-fat diet is likely to induce obesity and T2D. Obese lifestyle is commonly seen in developed countries and is gradually observed in developing countries as well. Obese lifestyle not only result in diabetes mellitus, but can also contribute to other chronically harmful disorders such as dyslipidemia, hyperlipidemia, hypertriglyceridemia, hypercholesterolemia, low high-density lipoprotein (HDL), and high low-density lipoprotein (LDL).

Currently, various natural polyphenolic compounds had been proven to counter inflammation, oxidation, cancer, and cardiovascular diseases. Resveratrol and curcumin, for instance, had been successfully used to prevent many metabolic syndromes. Although caffeic acid and caffeic acid phenylethyl amide (CAPA) had been reported with potent antidiabetic activity, such as exhibiting hypoglycemic properties, their effects on lipid metabolism and antihyperlipidemic activity remain unknown.

Some side effects like increased blood pressure/heart rate, insomnia, nervousness, restlessness, dependence, headache, nausea, dizziness, fatigue, etc, had known from administrating the existing medicament for metabolic syndromes. On the other hand, since most of the treatments for metabolic syndromes, such as obesity, hyperlipidemia, diabetes mellitus, etc. require patient's self-management on either medications, diet, or exercise, in order to seek control of certain parameters in blood including glucose, lipid, triglyceride, etc, patient's compliance or adherence with treatments may be problematic. In light of these, the development of a safe, effective, and economic pharmaceutical composition capable of ameliorating or remedying hyperlipidemia or other related metabolic syndromes is of crucial necessity.

SUMMARY OF THE INVENTION

As a result, the present invention provides a method of treating or preventing hyperlipidemia in a subject in need thereof, comprising administrating to the subject a therapeutically effective amount of the compound of Formula I:

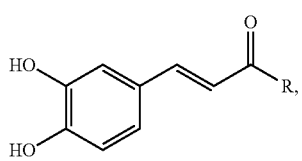

Formula I wherein R is selected from the group consisting of

n=4 or 5, $NH(CH_2)_2Ph$, $NHC_8H_{17}$, $NH(CH_2)_2$-m-Ph-F and $NH(CH_2)_2OH$.

In one embodiment of the present invention, the compound of Formula I suppresses high-fat diet-induced increase of triglyceride concentration in blood as well as suppresses high-fat diet-induced increase of free fatty acid concentration in blood.

In one embodiment of the present invention, the compound of Formula I decreases a hypertrophy of an adipocyte and a hepatocellular balloing phenomenon, wherein the adipocyte is from epididymal white adipose tissue (EWAT), mesenteric white adipose tissue (MWAT), retroperioneal white adipose tissue (RWAT), or visceral fat.

In one embodiment of the present invention, the compound of Formula I reduces high-fat diet-induced increase of a body weight gain. And in another embodiment of the present invention, the compound of Formula I increases the contents of phosphorylation of phosph-5' adenosine monophosphate-activated protein kinase (phospho-AMPK) in muscle and liver. Preferably, the muscle is a skeletal muscle. The compound of Formula I also decreases a level of leptin in blood and increases a level of adiponectin in blood. For the present invention, the therapeutically effective amount is at least 0.01 g/kg/day.

Another aspect of the present invention is to provide a pharmaceutical composition comprising the compound of Formula I:

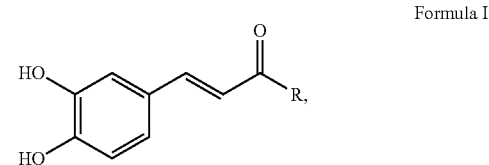

Formula I wherein R is selected from the group consisting of

n=4 or 5, $NH(CH_2)_2Ph$, $NHC_8H_{17}$, $NH(CH_2)_2$-m-Ph-F and $NH(CH_2)_2OH$. The pharmaceutical composition of the present invention further comprises a pharmaceutically acceptable carrier, excipient, diluent, adjuvant, medium, or combinations thereof. In one embodiment of the present invention, when R is

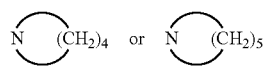

a half-life of the pharmaceutical composition is prolonged.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

DETAILED DESCRIPTION OF THE PREFERRED EMBODIMENT

Definition

Figure 1:
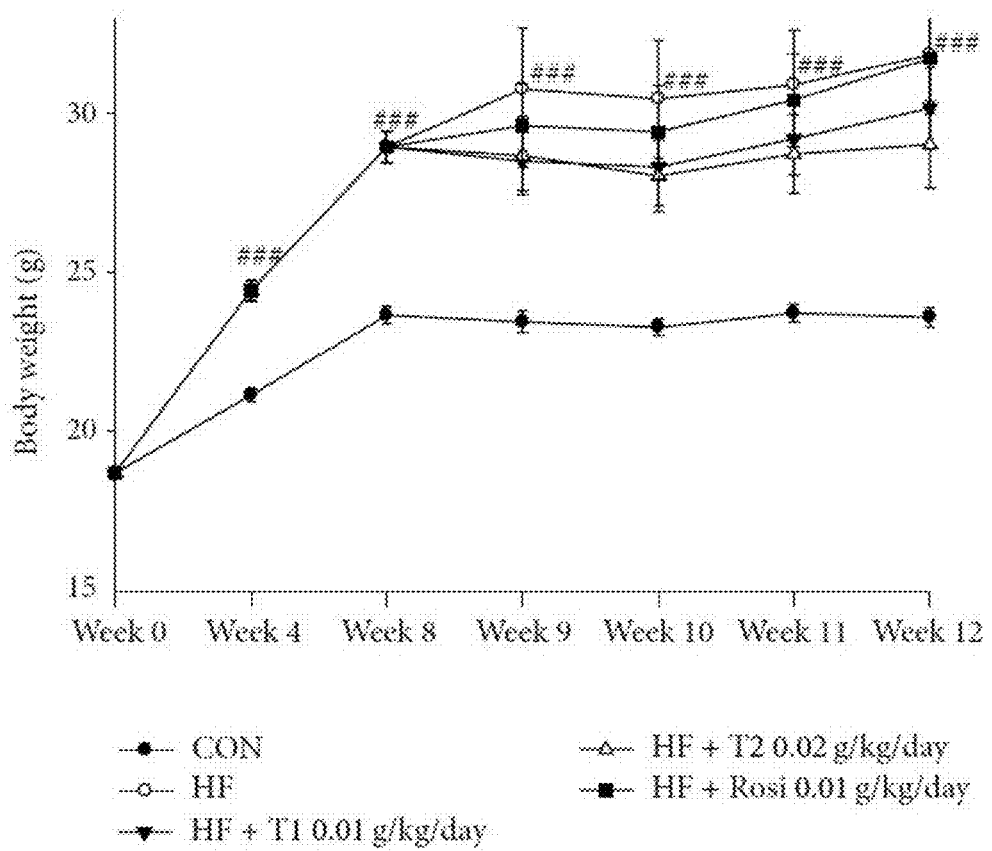
FIG. 1, effects of the caffeamide derivatives of the present invention on body weight. All values are means±S. E. (n=9). ####$P<0.001$ indicates result compared with the control CON group by ANOVA.

As used herein, the phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The term "pharmaceutically acceptable carrier" as used herein, refers to a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The embodiment of the present invention is to demonstrate the synthesis of the caffeamide derivatives of the present invention. Then, a high-fat diet-fed mice model is established and is use for determination and evaluation of high-fat diet-induced change of body weight, plasma/hepatic lipid, size of adipocyte/hepatocyte, and 5' adenosine monophosphate-activated protein kinase (AMPK) activation.

The abovementioned method is explained in detail as follow:

Materials and Method

Preparation of Caffeamide Derivatives

Firstly, to a two-neck bottle, 100 mg of caffeic acid is dissolved in 1 mL N,N-dimehylformamide and 0.08 mL triethylamine (1 mol). The solution is then added into 5 mL dichloromethane ($CH_2Cl_2$, 1.2 mol) containing piperidine (or phenylethylamine, or octylamine, or pyrrolide, or m-florophenylethylamine, or ethanolamine) and benzotriazol-1-yloxytris(dimethylamino)phosphonium hexafluorophosphate (BOP, 1.2 mol) for a 30-minute reaction at 0° C. followed by another 2-hour reaction at room temperature. After the reactions are finished, $CH_2Cl_2$ is removed. The resulting solution is then added into 50 mL water and extracted using ethyl ester. The organic phase is collected and washed with 1 mol HCl, 1 mol $NaHCO_3$, and water. After washing, the organic phase is further recollected and the water is removed therefrom by $MgSO_4$. The recollected organic phase is then subjected to filtration, condensation and column chromatography. Consequently, a compound of Formula Ia, (E)-3-[3,4-dihydroxyphenyl-1-(piperidin-1-yl) prop-2-en-1-one, was obtained as white solid. (yield: 75%)

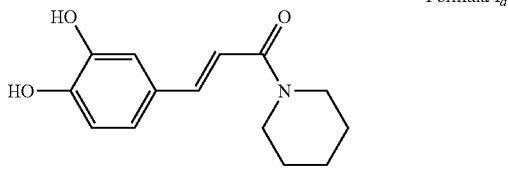

Formula $I_a$

Certain physical and chemical properties of the compound of Formula $I_a$ are listed as follow: melting point (mp): 144-146° C.; IR$\nu_{max}$ (cm$^{-1}$): 3431, 3115, 3061, 1651, 1618, 1593, 1506, 1423, 1278, 1244, 1045; $^1$H NMR (CD$_3$COCD$_3$, 400 MHz): δ 1.54-1.64 (6H, m), 3.53 (2H, t, J=6.8 Hz), 3.66 (2H, t, J=6.8 Hz), 6.82 (1H, d, J=8.2 Hz), 6.96, 7.43 (each 1H, d, J=15.2 Hz), 7.01 (1H, dd, J=8.2, 1.6 Hz), 7.14 (1H, d, J=1.6 Hz); UV (MeOH) $\lambda_{max}$ (log ε): 325 (4.32), 291 (4.19), 2.30 (4.26), 2.19 (4.50) nm; HRESIMS m/z: 270.1106 [M+Na]$^+$ (calcd. for C$_{14}$H$_{17}$NO$_3$Na, 270.1109).

Similarly, a compound of Formula $I_b$ is synthesized to give a solid as in the preparation method set forth above, with functional group of NH(CH$_2$)$_2$Ph.

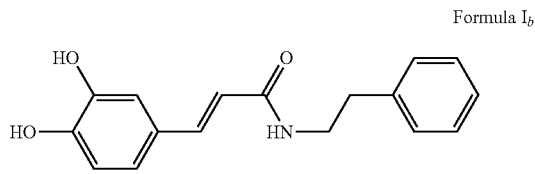 [SMILES: O=C(/C=C/c1ccc(O)c(O)c1)NCCc1ccccc1]

Formula $I_b$

Certain physical and chemical properties of the compound of Formula $I_b$ are listed as follow: melting point (mp): 148-149° C.; IR$\nu_{max}$ (cm$^{-1}$): 3288, 1642, 1591, 1523, 1631, 1279, 1036, 975, 849; $^1$H NMR (CD$_3$COCD$_3$, 500 MHz): δ 2.84 (2H, t, J=6.8 Hz), 3.53 (2H, q, J=6.8 Hz), 6.43 (1H, d, J=15.2 Hz), 6.83 (1H, d, J=8.1 Hz), 6.92 (1H, dd, J=8.1, 1.8 Hz), 7.07 (1H, d, J=1.8 Hz), 7.15-7.30 (5H, m), 7.35 (—NH, br. s), 7.43 (1H, d, J=15.2 Hz), 8.20 (—OH, s); EI-MS m/z (%): 283 (M$^+$, 17), 178 (22), 163 (100); UV (MeOH) $\lambda_{max}$ (log ε): 322 (4.42), 296 (4.36), 2.45 (4.30), 216 (4.61) nm.

Similarly, a compound of Formula I is synthesized to give a white solid as in the preparation method set forth above, with functional group of NHC$_8$H$_{17}$.

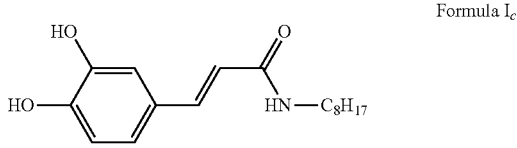

Formula $I_c$

Certain physical and chemical properties of the compound of Formula $I_c$ are listed as follow: melting point (mp): 111-112° C.; IR$\nu_{max}$ (cm$^{-1}$): 3286, 1642, 1588, 1520, 1363, 1277, 1112, 975, 811; $^1$H NMR (CD$_3$COCD$_3$, 400 MHz): δ 0.84 (3H, t, J=6.6 Hz), 1.24 (10H, m), 1.52 (2H, quin, J=6.6 Hz), 3.30 (2H, q, J=6.6 Hz), 6.47, 7.42 (each 1H, d, J=15.6 Hz), 6.82 (1H, d, J=8.2 Hz), 6.90 (1H, dd, J=8.2, 1.8 Hz), 7.09 (1H, d, J=1.8 Hz); EI-MS m/z (%): 291 (M$^+$, 18), 220 (8), 193 (11), 178 (31), 163 (100), 145 (8), 135 (13), 128 (22), 98 (8), 89 (19), 84 (12); UV (MeOH) $\lambda_{max}$ (log ε): 324 (4.32), 294 (4.26), 238 (3.92), 2.19 (4.37) nm.

Similarly, a compound of Formula $I_d$ is synthesized to give a white solid as in the preparation method set forth above, with functional group of

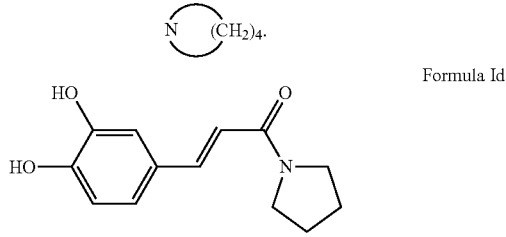

Formula Id

Certain physical and chemical properties of the compound of Formula $I_d$ are listed as follow: melting point (mp): 174-176° C.; IR$\nu_{max}$ (cm$^{-1}$): 3442, 3093, 3041, 1693, 1598, 1564, 1531, 1436, 1300, 1278, 1184, 956; $^1$H NMR (CD$_3$COCD$_3$, 400 MHz): δ 1.79-1.89 (4H, m), 3.44 (2H, t, J=6.8 Hz), 3.66 (2H, t, J=6.8 Hz), 6.70, 7.42 (each 1H, d, J=15.4 Hz), 6.82 (1H, d, J=8.0 Hz), 6.99 (1H, d, J=8.0 Hz), 7.13 (1H, s); UV (MeOH) $\lambda_{max}$ (log ε): 324 (4.12), 287 (4.21), 252 (4.23), 206 (4.32) nm; HRESIMS m/z: 256.0953 [M+Na]$^+$ (calcd. for C$_{14}$H$_{17}$NO$_3$Na, 256.0950).

Similarly, a compound of Formula $I_e$ is synthesized to give a white solid as in the preparation method set forth above, with functional group of NH(CH$_2$)$_2$-m-PhF.

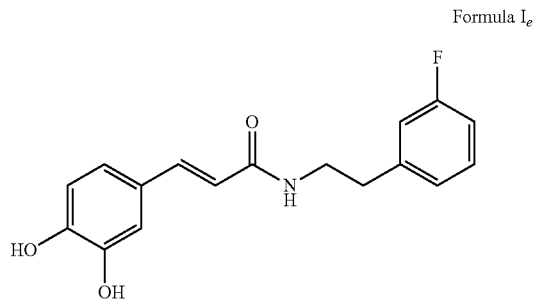 [SMILES: O=C(/C=C/c1ccc(O)c(O)c1)NCCc1cccc(F)c1]

Formula $I_e$

Certain physical and chemical properties of the compound of Formula $I_e$ are listed as follow: Colorless crystal (MeOH); mp 155-157° C.; IR$\nu_{max}$ (cm$^{-1}$): 3503, 3352, 3179, 1647, 1589, 1535, 1489, 1443, 1361, 1304, 1273, 1121, 1184, 968; $^1$H NMR (CD$_3$OD, 500 MHz): δ 7.38, 6.33 (1H each, d, J=15.6 Hz), 7.28 (1H, td, J=7.9, 6.2 Hz), 7.05 (1H, d, J=7.7 Hz), 6.99 (1H, d, J=2.0 Hz), 6.98 (1H, brd, J=9.9 Hz), 6.92 (1H, td, J=8.3, 2.5 Hz), 6.89 (1H, dd, J=8.1, 2.0 Hz), 6.76 (1H, d, J=8.1 Hz), 3.51, 2.81 (2H each, t, J=7.2 Hz); UV (MeOH) $\lambda_{max}$ (log ε): 323 (4.53), 295 (4.46), 239 (4.43), 216 (4.62) nm; HRESIMS m/z 324.1014 [M+Na]$^+$ (calcd for C$_{17}$H$_{16}$FNO$_3$Na, 324.1012)

Similarly, a compound of Formula $I_f$ is synthesized as to give a white solid as in the preparation method set forth above, with functional group of NH(CH$_2$)$_2$OH.

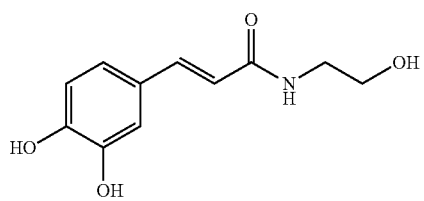

Formula I$_f$

Certain physical and chemical properties of the compound of Formula I$_f$ are listed as follow: Yellowish crystal (MeOH); mp 189-191° C.; IRv$_{max}$ (cm$^{-1}$): 3429, 3341, 3170, 1651, 1604, 1585, 1543, 1303, 1269, 1207, 1061; $^1$H NMR (CD$_3$OD, 500 MHz): 7.40, 6.39 (1H each, d, J=15.7 Hz), 7.01 (1H, d, J=2.0 Hz), 6.90 (1H, dd, J=8.2, 2.0 Hz), 6.77 (1H, d, J=8.2 Hz), 3.65, 3.41 (2H each, t, J=5.8 Hz); $^{13}$C NMR (CD$_3$OD, 125 MHz): 169.8, 148.9, 146.9, 142.5, 128.5, 122.3, 118.5, 116.6, 115.2, 61.9, 43.3; UV (MeOH) $\lambda_{max}$ (log ε): 323 (4.24), 295 (4.18), 232 (4.23), and 217 (4.39) nm; HRESIMS m/z 246.0745 [M+Na]$^+$ (calcd for C$_{11}$H$_{13}$NO$_4$Na, 246.0742)

Experimental Animals and Design

All animal procedures were performed as per guidelines provided by the Institutional Animal Care and Use Committee of Central Taiwan University of Science and Technology. Firstly, C57BL/6J mice (4-5 weeks old) were purchased from the National Laboratory Animal Breeding and Research Center, National Science Council, Taiwan, and were maintained on a 12-hour light/dark cycle (light cycle: 7 a.m. to 7 p.m.). Seven days after acclimation, the C57BL/6J mice were divided randomly into two groups: the control group (CON, n=9) was fed with low-fat diet (Diet 12450B, Research Diets, Inc., New Brunswick, N.J. 08901, USA), whereas the experimental group (n=36) was fed with a 45% high-fat diet (Diet 12451, Research Diets, Inc., New Brunswick, N.J. 08901, USA) for 12 weeks. The low-fat diet was composed of protein 20%, carbohydrate 70% and fat 10%, whereas the high-fat diet was composed of protein 20%, carbohydrate 35%, and fat 45% (of total energy, % kcal). After 8-week diet-induction period, the high-fat treated mice were randomly subdivided into four groups (n=9 per group), namely, control group (CON), high-fat control group (HF), TS group (including T1 and T2, representing mice treated with the compound of the present invention using a dosage of 10 mg/kg/day and 20 mg/kg/day, respectively), rosiglitazone treated group (Rosi; 1% methylcellulose 10 mg/kg body weight, obtained from GlaxoSmithKline, product number: BRL49653 C). TS and Rosi group were administrated through oral gavage one time per day from the 9$^{th}$ to the 12$^{th}$ week of the experiment while the mice were still on the high-fat diet. On the other hand, CON and HF groups were treated with vehicle only. The body weight was measured weekly throughout the experimentation. By the end of the experimentation, food was deprived from the mice (from 10 p.m. to 10 a.m.) On the next day (the 85$^{th}$ day), all mice were sacrificed for blood and tissue collection and analysis. The mice were untreated with TS or Rosi at the 85$^{th}$ day. Livers and white adipose tissue (WATs, including epididymal mesenteric, and retroperitoneal WAT) were excised according to the defined anatomical landmarks, and the weight of the tissues was measured. Tissues were immediately frozen using liqid nitrogen and then kept at −80° C. for the analysis of target gene expression. Heparin (30 units/mL, Sigma) was added into blood sample. Plasma samples were collected by centrifugation at 1600 g×g for 15 minutes at 4° C. The separation of the plasma was finished within 30 minutes. Plasma was obtained for leptin assay.

Blood Parameters Assay and Measurement of Hepatic Lipids

Blood samples (0.8 mL) were collected from the retroorbital sinus of fasting mice and the plasma triglycerides (TG), total cholesterol (TC), and free fatty acids (FFA) were analyzed using commercial assay kits according to the manufacture's directions (Triglycerides-E test, Cholesterol-E test, and FFA-C test, Wako Pure Chemical, Osaka, Japan).

The levels of adiponectin and leptin were analyzed by ELISA using commercial assay kits according to manufacture's directions (mouse/rat adiponectin ELISA kit, B-Bridege International, GmbH, Germany, and mouse leptin ELISA kit, Morinaga, Yokohama, Japan).

For hepatic lipid extraction, a 0.375 g liver samples were homogenized with 1 mL distill water for 5 minutes. The dried pellet was finally resuspended in 0.5 mL ethanol and analyzed using a triglycerides kit as used for analyzing the serum lipids set forth above.

Histopathology of Adipose and Liver Tissue

Small pieces of epididymal white adipose tissue and liver tissue were fixed with formalin (200 g/kg) neutral buffered solution and embedded in paraffin. Sections of 8 m in diameter were cut and stained with hematoxylin and eosin. For microscopic examination, a microscope (Leica, DM2500) was used, and the images were taken using a Leica Digital Camera (DFC-425-C).

Isolation of RNA and Relative Quantization of mRNA Indicating Gene Expression

Total RNA from liver tissue was isolated with a Trizol Reagent (Molecular Research Center, Inc., Cincinnati, Ohio) according to the manufacture's directions. The integrity of the extracted total RNA was examined by 2% agarose gel electrophoresis, and the RNA concentration was determined by the ultraviolet (UV) light absorbency at 260 nm and 280 nm (Spectrophotometer U-2800A, Hitachi). The quality of the RNA was confirmed by ethidium bromide staining of 18S and 28S ribosomal RNA after electrophoresis on 2% agarose gel containing 6% formaldehyde. Total RNA (1 µg) was reverse transcribed to cDNA in a reaction mixture containing buffer, 2.5 mM dNTP (Gibco-BRL, Grand Island, N.Y.), 1 mM oligo (dT) primer, 50 mM dithiothreitol, 40 U Rnase inhibitor (Gibco-BRL, Grand Island, N.Y.), and 5 µL Moloney murine leukemia virus reverse transcriptase (TEpicentre, Madison, Wis., USA) at 37° C. for 1 hour and then heated at 90° C. for 5 minutes to terminate the reaction. The polymerase chain reaction (PCR) was performed in a final 25 µL containing 1 U Blend Taq-Plus (TOYOBO, Japan), 1 µL of the RT first-strand cDNA product, 10 M of each forward (F) and reverse (R) primer, 75 mM Tris-HCL (pH 8.3) containing 1 mg/L Tween 20, 25 mM dNTP, and 2 mM MgCl$_2$. Preliminary experiments were carried out with various cycles to determine the nonsaturating conditions of the PCR amplification for all the genes studied. The primers used are shown in Table 1. The products were run on 2% agarose gels and stained with ethidium bromide. The relative density of the band was evaluated using AlphaDigiDoc 1201 software (Alpha Innotech Co., San Leandro, Calif., USA). All the measured PCR products were normalized to the amount of cDNA of GAPDH in each sample.

TABLE 1

| Gene | Accession numbers | Forward primer and Reverse primer | PCR product (bp) | Annealing temp- erature (° C.) |
|---|---|---|---|---|
| FAS | NM_007988 | F: TGGAAAGATAA CTGGGTGAC (SEQ ID NO: 1) R: TGCTGTCGTCT GTAGTCTTG (SEQ ID NO: 2) | 240 | 50 |
| apo C-III | NM_023114.3 | F: CAGTTTTATCC CTAGAAGCA (SEQ ID NO: 3) R: TCTCACGACTC AATAGCTG (SEQ ID NO: 4) | 349 | 47 |
| Adipo- nectin | NM_009605.4 | F: TCTTCTACAAC CAACAGAATCA (SEQ ID NO: 5) R: GTATCATGGTA GAGAAGGAAGC (SEQ ID NO: 6) | 324 | 50.5 |
| GAPDH | NM_031144 | F: TGTGTCCGTCG TGGATCTGA (SEQ ID NO: 7) R: CCTGCTTCACC ACCTTCTTGA (SEQ ID NO: 8) | 99 | 55 |

Western Immunoblotting Analysis

Protein extractions and immunoblots for the determination of phospho-AMPK (Thr172) and phospho-Akt (Ser 473) proteins were carried out on frozen skeletal muscle and liver tissue form mice. Briefly, samples (0.1 g) were powdered under liquid nitrogen and homogenized for 20 seconds in 500 µL buffer containing 20 mM Tris-HCL1 (pH 7.4 at 4° C.), 2% SDS, 5 mM EDTA, 5 mM EGTA, 1 mM DTT, 100 mM NaF, 2 mM sodium vanadate, 0.5 mM phenylmethylsulfonyl fluoride, 10 µg/mL leupeptin, and 10 µL/mL pepstatin. 40 µg of each homogenate was mized with an equal amount of 2× standard SDS sample loading buffer containing 125 mM Tris-HCl (pH 6.8), 4% SDS, 20% glycerol, 10% 3-mercaptoethanol, and 0.25% bromophenol blue and boiled for 10 minutes before electrophoresis. The protein contents of phospho-AMPK (Abcam Inc., Cambridge, Mass., USA) and phospho-Akt (Cell signaling Technology, Inc., Danvers, Mass., USA) were detected by immunoblotting using a rabbit polyclonal antibody. About 0.1 g of liver tissue and skeletal muscle of mice (n=9) was used for the homogenate samples containing lysis buffer (pH 6.4) and protease inhibitors. The protein concentration in supernatant was determined with a BCA protein assay kit (Thermo Scientific, Rockford, Ill., USA). 20 µg of proteins were separated by electrophoresis on a polyacrylamide gel 10% (SDS-PAGE) and transferred to a nitrocellulose membrane. The membranes were blocked with 5% slim milk in Tris-buffered saline (TBS)(Amersham BioSciences, Uppsala, Sweden) containing 0.05% Tween-20 (Bio Rad, CA, USA) and incubated overnight at 4° C. with anti-phospho-AMPK and anti-phospho-Akt at 1:200 dilution. Subsequently, the membranes were washed three times with TBS containing 0.05% Tween-20 and incubated with secondary antibody anti-rabbit (1:1000) (Jackson ImmunoResearch Laboratories, Inc., PA, USA) for 1 hour. Immunoreactive bands were detected with ECL reagent kit (GE Healthcare BioSciences, Buckinghamshire, UK). The density blotting was analyzed using Alpha Easy FC software (Alpha Innotech Corporation, Randburg, South Africa). Structural proteins GAPDH (Santa Cruz Biotechnology, CA, USA) were obtained by stripping the nitrocellulose membrane proteins of liver and skeletal muscle.

Statistical Analysis

The data represented herein are expressed as mean±S.E. values. Whenever possible, data were subjected to analysis of variance, followed by Dunnett's multiple range tests using SPSS software (SPSS Inc., Chicago, Ill., USA). $P<0.05$ was considered to exhibit statistical significance.

Example 1

Caffeamide Derivatives Reduce High-Fat Diet-Induced Increase of a Body Weight Gain Body weight of mice was monitored and measured daily at the same time throughout the experimentation. The differences between the body weight of the next day and the former day is defined as body weight gain. The pellet food was weighed and followed by being placed in the cage food container. Unconsumed pellet high-fat food was discarded each day and fresh pellet of high-fat diet was provided to ensure consistent food quality throughout the experimentation. The high-fat food was stored at 4° C.

All group mice stared with similar mean body weights (1.76±0.2 g). After 8 weeks breeding as indicated above, the HF group was treated with vehicle or TS or rosiglitazone (Rosi) accompanied with high-fat diet for 4 weeks. As shown in FIG. 1, in the first 8 weeks, the body weight increased significantly for all mice receiving high-fat diet as compared to the CON group. In week 8 to 12, T1 and T2 treated mice shown reduced body weight compare with both the HF group and the HF+Rosi group. Meanwhile, as shown in Table 2, at week 12, the body weight gain of the HF group is greater than the CON group (P<0.01), while the T2-treated group decreased in body weight gain significantly compared with the HF group (P<0.05). When treated with T1, T2, and Rosi, a significant decrease in the weights of absolute epididymal white adipose tissue (EWAT), visceral fat, mesenteric white adipose tissue (MWAT), and retroperitoneal white adipose tissue (RWAT) can be observed compared with the HF group. The weight of brown adipose tissue (BAT) is also decreased in T2-treated mice as compared with the HF group (P<0.05).

TABLE 2

| Parameter | CON | HF | HF + T1 (0.01 g/kg/day) | HF + T2 (0.02 g/kg/day) | HF + Rosi (0.01 g/kg/day) |
|---|---|---|---|---|---|
| | | Absolute tissue weight(g) | | | |
| EWAT | 0.349 ± 0.003 | 1.481 ± 0.158### | 0.999 ± 0.105* | 0.832 ± 0.082*** | 1.003 ± 0.103* |
| MWAT | 0.278 ± 0.014 | 0.518 ± 0.070### | 0.406 ± 0.016** | 0.372 ± 0.025*** | 0.238 ± 0.033*** |
| RWAT | 0.087 ± 0.010 | 0.671 ± 0.059### | 0.472 ± 0.065* | 0.373 ± 0.050** | 0.334 ± 0.057* |
| Visceral fat | 0.429 ± 0.027 | 2.148 ± 0.198### | 1.471 ± 0.166** | 1.205 ± 0.130*** | 1.330 ± 0.138*** |

TABLE 2-continued

| Parameter | CON | HF | HF + T1 (0.01 g/kg/day) | HF + T2 (0.02 g/kg/day) | HF + Rosi (0.01 g/kg/day) |
|---|---|---|---|---|---|
| | | Absolute tissue weight(g) | | | |
| BAT | 0.127 ± 0.025 | 0.191 ± 0.023 | 0.162 ± 0.042 | 0.121 ± 0.014* | 0.210 ± 0.023 |
| Weight gain (g) | −0.12 ± 0.31 | 2.61 ± 1.04## | 1.71 ± 0.59 | 0.43 ± 0.59* | 0.91 ± 1.45 |

All values are means ± S.E. (n = 9).
$p < 0.05$,
$p < 0.01$,
$p < 0.001$ compared with the control group (CON);
*$P < 0.05$,
**$P < 0.01$,
***$P < 0.001$ compared with the high-fat + vehicle (distilled water) (HF) group.

Hence, it is demonstrated that the caffeamide derivatives of the present invention can reduce the absolute tissue weight and body weight gain of mice fed with high-fat diet, and such reducing effect is better when treated with dosage of 0.02 g/kg body weight, indicating a dosage-dependent correlation. It is also noted that the daily dosage is expected to have an accumulative effect and long-lasting effectiveness due to the caffeamide derivatives of the present invention being, for example, one of 3° amides, which is not easy to cut off the structure. Consequently, the pharmaceutical composition containing the same exhibits a prolonged half-life.

Example 2

Caffeamide Derivatives Suppress High-Fat Diet-Induced Increase of Plasma and Hepatic Lipid As shown in Table 3, at week 12, the levels of total cholesterol (TC), triglyceride (TG), and free fatty acid (FFA) were greater in the HF group than in the CON group ($P<0.001$, $P<0.001$, and $P<0.01$, respectively). The T1-, T2-, and Rosi-treated groups suppressed the HF diet-induced increases in the concentration of TG ($P<0.01$, $P<0.001$, and $P<0.05$, respectively), while treatment with T1, T2, and Rosi suppressed the high-fat diet-induced increases in the concentration of FFA ($P<0.01$, $P<0.001$, and $P<0.05$, respectively). The results demonstrated that the caffeamide derivatives of the present invention can suppress the high-fat diet-induced increase of triglyceride concentration and free fatty acid concentration in blood.

As for the leptin and adiponectin concentrations, at week 12, T1-, T2-, and Rosi-treated groups show significant decreases of leptin concentration in blood ($P<0.001$, $P<0.001$, and $P<0.001$, respectively) compared with the HF group, whereas the adiponectin levels in blood of the T1-, T2-, and Rosi-treated groups are increased ($P<0.05$, $P<0.01$, and $P<0.01$, respectively) compared with the HF group. As leptin and adiponectin were known to regulate energy balance and fatty acid breakdown, respectively, the result indicated that the caffeamide derivatives of the present invention can promote secretion or gene expression of adiponectin and decrease the level of leptin; thus, enhances the suppression of high-fat diet-induced increase of plasma and hepatic lipid.

In regard to the liver lipids, as shown in Table 3, when treated with T1, T2, and Rosi, the total lipid as well as the concentration of triacylglycerol is significantly reduced, indicating that the caffeamide derivatives of the present invention can not only suppress the high-fat diet-induced increase of triglyceride concentration and free fatty acid concentration in blood but also reduce the lipid content in liver.

TABLE 3

| Parameter | CON | HF | HF ± T1 (0.01 g/kg/day) | HF ± T2 (0.02 g/kg/day) | HF + Rosi (0.01 g/kg/day) |
|---|---|---|---|---|---|
| | Blood profiles | | | | |
| TG (mg/dL) | 56.4 ± 4.1 | 107.4 ± 5.8### | 77.5 ± 5.8** | 75.9 ± 4.7*** | 81.8 ± 5.8* |
| FFA (meq/L) | 1.64 ± 0.08 | 2.68 ± 0.07## | 1.32 ± 0.14** | 1.27 ± 0.09*** | 1.52 ± 0.16* |
| TC (mg/dL) | 91.0 ± 4.7 | 183.4 ± 6.8### | 175.0 ± 7.0 | 184.9 ± 23.8 | 134.9 ± 3.5 |
| Adiponectin (ng/mL) | 7.12 ± 0.31 | 4.39 ± 0.22## | 6.72 ± 0.37* | 7.35 ± 0.49** | 7.51 ± 0.53** |
| Leptin (µg/mL) | 1.230 ± 0.062 | 2.923 ± 0.056### | 2.155 ± 0.100*** | 2.009 ± 0.105*** | 2.063 ± 0.111*** |
| | Liver lipids | | | | |
| Total lipid (mg/g) | 51.0 ± 3.6 | 91.1 ± 5.2### | 69.8 ± 3.7* | 60.2 ± 5.9** | 60.2 ± 5.4** |
| Triacylglycerol (µmol/g) | 30.1 ± 3.3 | 74.4 ± 6.8### | 53.6 ± 5.6* | 46.1 ± 6.2** | 42.6 ± 5.8** |

All values are means ± S.E. (n = 9).
$p < 0.05$,
$p < 0.01$,
$p < 0.001$ compared with the control group (CON);
*$P < 0.05$,
**$P < 0.01$,
***$P < 0.001$ compared with the high-fat + vehicle (distilled water) (HF) group.

Example 3

Figure 2A:
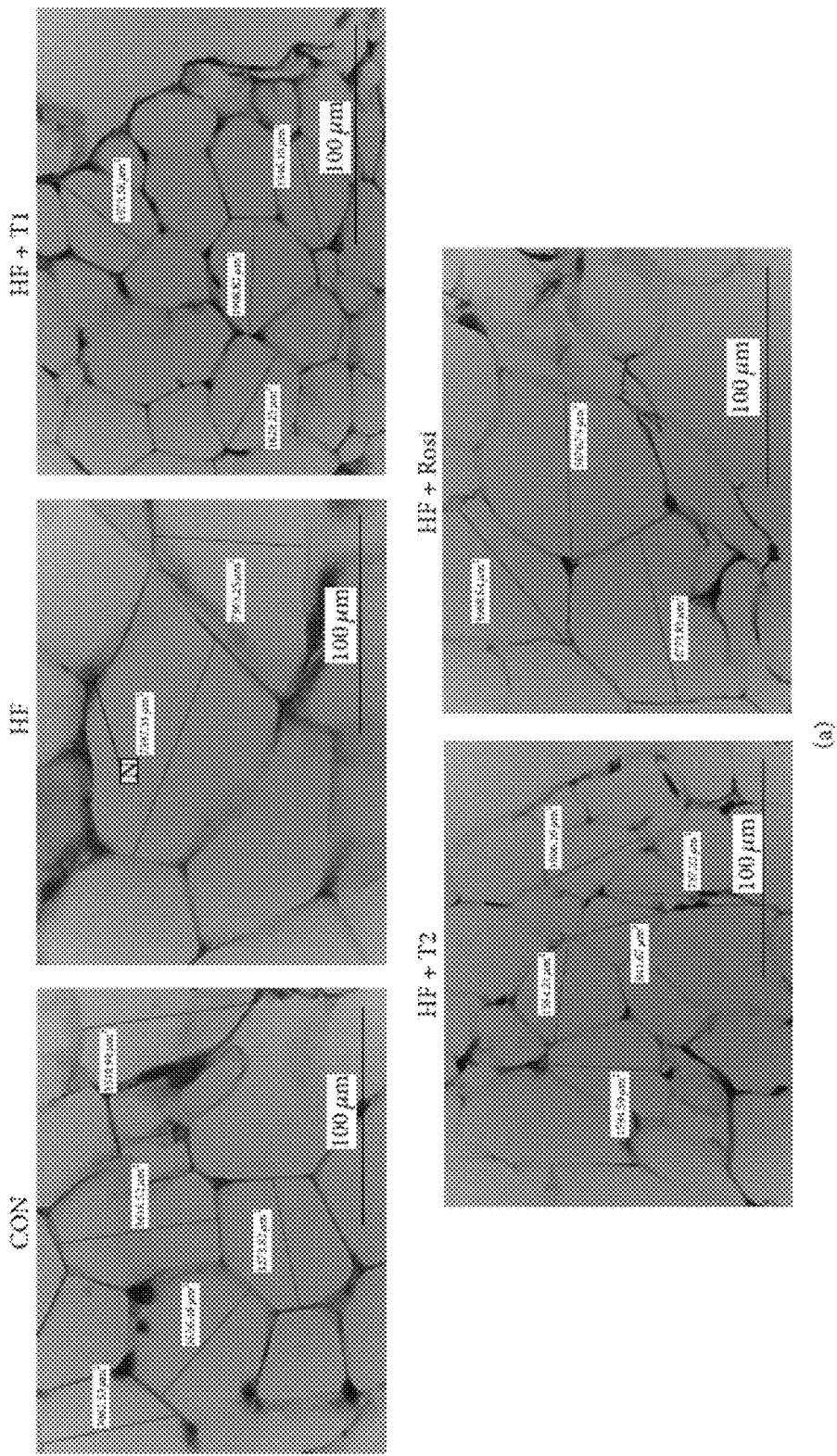
FIG. 2(a), mean area of adipocytes ($\mu m^2$) from epididymal white adipose tissue (magnification: 10 (ocular)×20 (object lens)) of mice with our without treating with the caffeamide derivatives of the present invention.

Caffeamide Derivatives Decreases the Hypertrophy of Adipocyte and Hepatocellular Ballooning Phenomenon As shown in FIG. 2(a), feeding with the high-fat diet induced hypertrophy of the adipocytes compared with the CON group in epididymal white adipose tissue. The average area of the cut of the adipocytes in the HF group (6765.87 μm) is larger than in the CON group (3263.78 μm). Treatments of T1 and T2 significantly decrease the size of the adipocytes to 1827.59 μm and 1651.31 μm, respectively, while the average area of the cut of the adipocytes in the Rosi-treated group is 4600.96 μm. Adipocyte, also known as white adipose tissue, is polyhedral by H&E stain, and the appearance showed sting-like cytosol surrounding a vacuole due to being embedded in paraffin as immersed in lipid solvents. Unobvious nucleus (N) can be observed in the other side of cells.

Figure 2B:
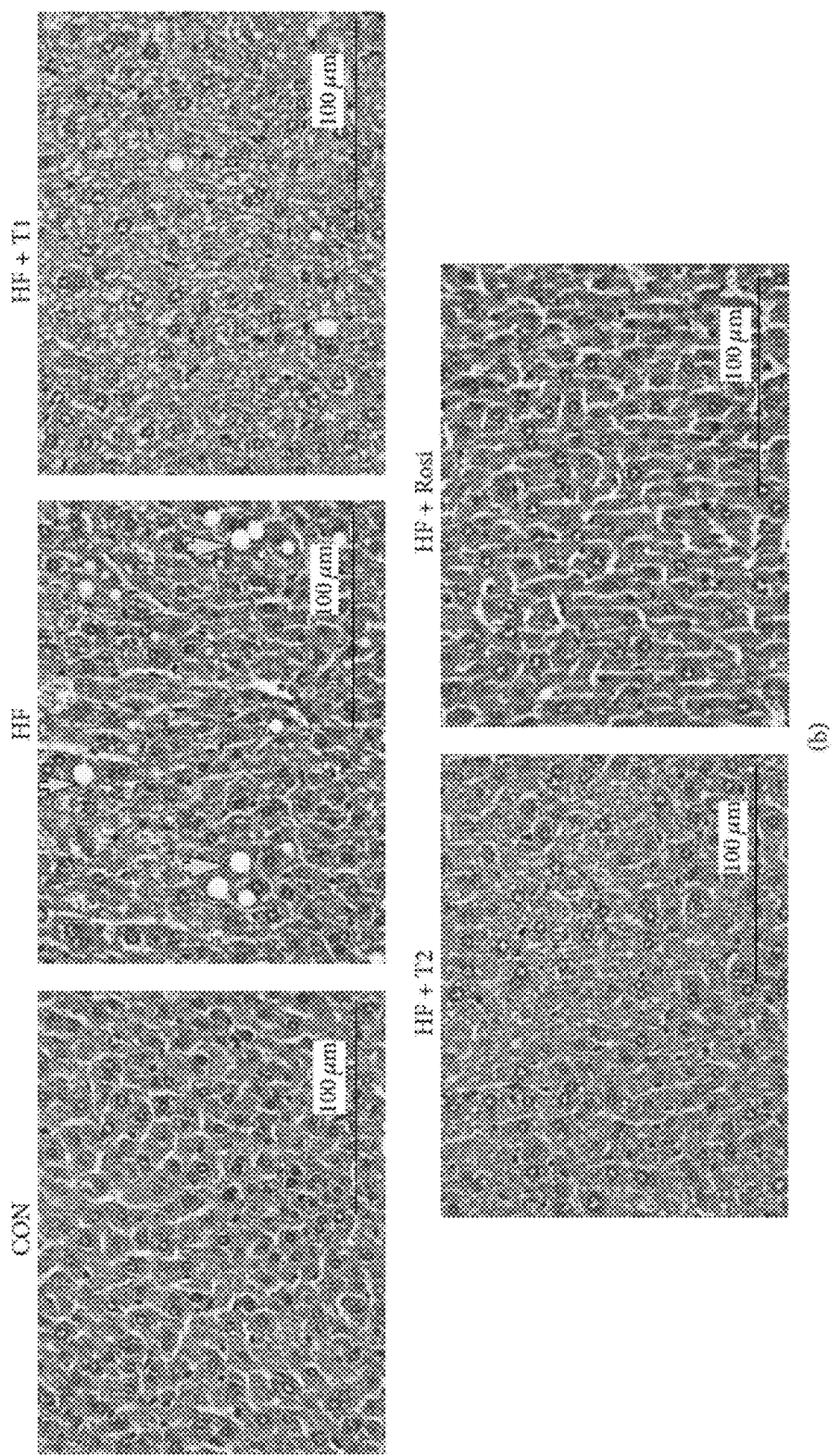
FIG. 2(b), liver tissue (magnification: 10 (ocular)×20 (object lens)) from mice with or without treating with the caffeamide derivatives of the present invention.

Ballooning degeneration is a form of liver parenchymal cell death and the nucleolus was squeezed into the other side named balloon (as indicated by arrow in FIG. 2(b)). As shown in FIG. 2(b), high-fat diet induced the ballooning of hepatocyte compared with the CON group in liver tissue. The histological hepatocellular ballooning findings is visible on HF diet. The ballooning phenomenon is lower in the T1-, T2-, and Rosi-treated mice, indicating that the caffeamide derivatives of the present invention can significantly decrease the degree of ballooning degeneration, which represents liver steatosis, in liver tissue.

In addition, it can be observed that the number of large adipocytes was decreased while the number of small adipocytes was increased by the treatment of the caffeamide derivatives of the present invention. Thus, it is suggested that the caffeamide derivatives of the present invention are able to mobilize fat from adipose tissue by increasing lipid catabolism in liver, since lipid that accumulate in adipose tissue are largely derived from circulating triglyceride and liver is a major target tissue for lipid and lipoprotein metabolism. In other words, the caffeamide derivatives of the present invention decrease the triglyceride synthesis in liver which effectively regulated morphometric adipocytes.

Example 4

Figure 3:
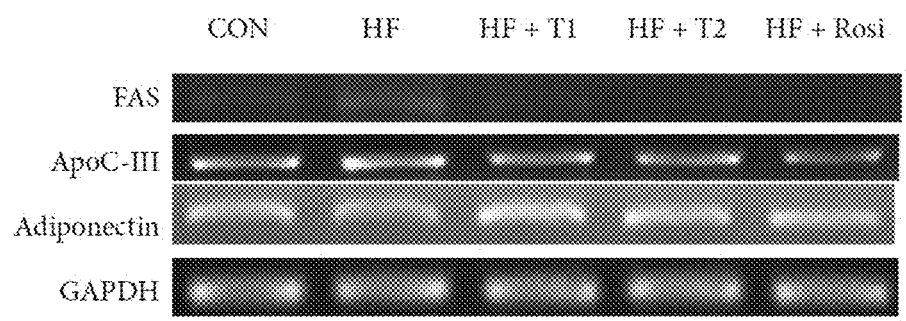
FIG. 3(a), image of gel electrophoresis of semiquantitative RT-PCR analysis on fatty acid synthase (FAS), apolipoprotein C-III (apo C-III), and adiponectin mRNA expression in liver tissue of mice orally gavage the caffeamide derivatives of the present invention. T1 indicates treatment with the caffeamide derivatives of the present invention at dosage of 10 mg/kg body weight; T2 indicates treatment with the caffeamide derivatives of the present invention at dosage of 20 mg/kg body weight; Rosi indicates treatment with rosiglitazone at dosage of 0.01 g/kg body weight.
FIG. 3(b), semiquantitative target mRNA expression in liver tissue of mice orally gavage the caffeamide derivatives of the present invention. All values are means±S. E. (n=9). ##$P<0.01$ and ###$P<0.001$ indicates results compared with the control (CON) group; *$P<0.05$, $P<0.01$, and *$P<0.001$ indicates results compared with the high-fat+ vehicle (HF) group. Signals were quantitated by image analysis; each value was normalized by GAPDH.
Figure 3B:
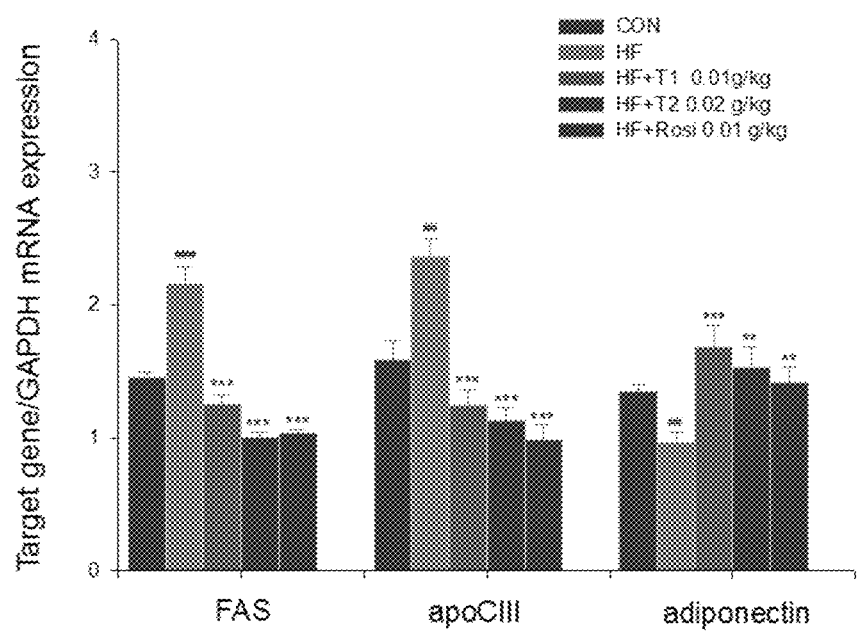

Caffeamide Derivatives Regulates the Phospho-AMPK (Thr172) Protein Content and the Phospho-Akt (Ser473)/Total Akt Protein Content 5' adenosine monophosphate-activated protein kinase (AMPK) is a major cellular regulator of lipid metabolism and the activation of AMPK result in increase lipid catabolism. Particularly, the phosphorylation of Thr172 of a subunits plays an important role in AMPK activity. Akt activation in liver contributes to suppression of gluconeogenesis. As shown in FIG. 3(a) and FIG. 3(b), at week 12, the mRNA levels of fatty acid synthase (FAS) and apolipoptroein C-III (apo C-III) were higher in the HF group than in the CON group ($P<0.001$ and $P<0.001$, respectively), whereas the expressions of adiponectin were lower in the HF group than in the CON group ($P<0.01$). Upon treatment of T1, T2, and Rosi, the T1-, T2-, and Rosi-treated groups showed decreased mRNA level of FAS and apo C-III compared with the HF group ($P<0.001$ and $P<0.01$, respectively). The mRNA level of adiponectin after treatment of T1, T2, and Rosi, on the other hand, was increased compared with the HF group ($P<0.01$). These results indicated that the caffeamide derivatives of the present invention can downregulate the mRNA expression of FAS and apo C-III but upregulate the mRNA level of adiponectin.

Figure 4A:
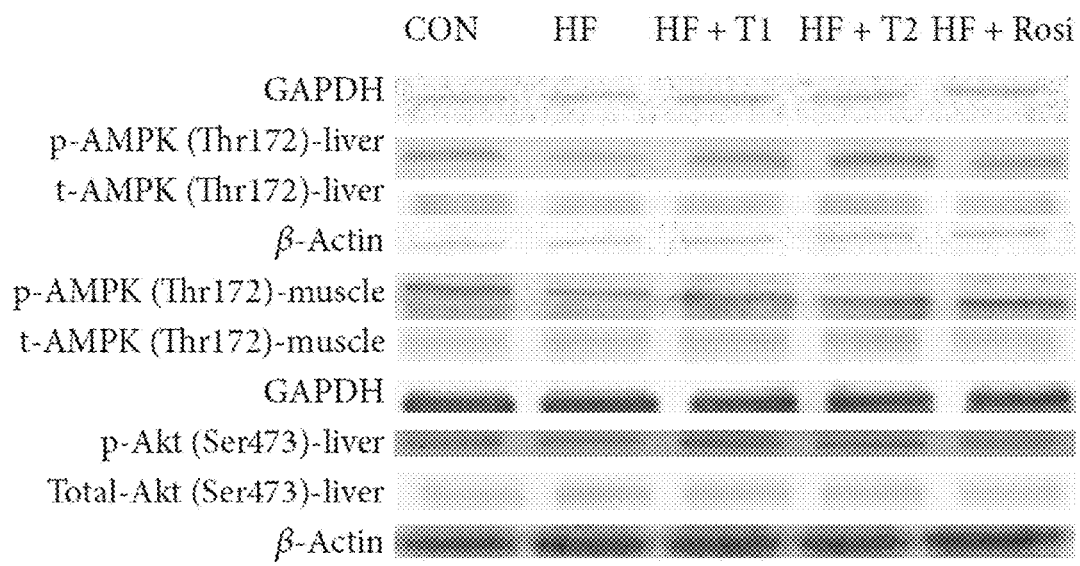
FIG. 4(a), image of western blotting of the ratio of phosphor-5' adenosine monophosphate-activated protein kinase (phosphor-AMPK) (Thr172) to total AMPK in liver tissue and skeletal muscle and the phosphorylation status of protein kinase B (Akt) (p-Akt normalized to total Akt (pAkt/tAkt)) in liver tissue. Activation of AMPK has been shown to increased lipid and glucose metabolism. T1 indicates treatment with the caffeamide derivatives of the present invention at dosage of 10 mg/kg body weight; T2 indicates treatment with the caffeamide derivatives of the present invention at dosage of 20 mg/kg body weight; Rosi indicates treatment with rosiglitazone at dosage of 0.01 g/kg body weight.
Figure 4B:
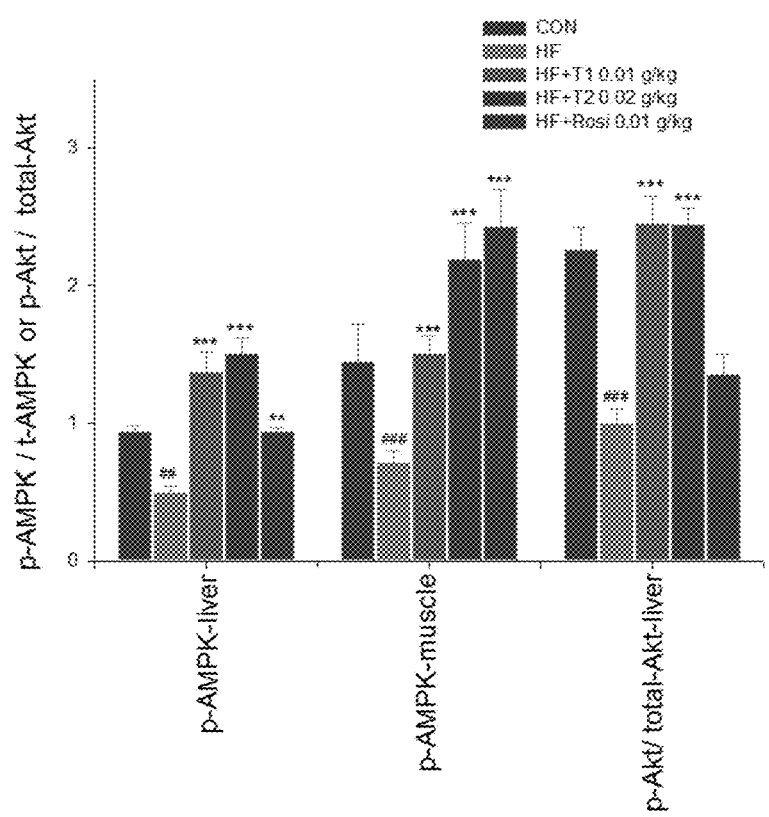
FIG. 4(b), quantification for phospho-AMPK in liver and muscle and phospho-Akt in liver. All values are means±S. E. (n=9). #$P<0.05$, ##$P<0.01$, and ###$P<0.001$ indicates results compared with the control (CON) group; *$P<0.05$, $P<0.01$, and *$P<0.001$ indicates results compared with the high-fat+vehicle (HF) group.

As shown in FIG. 4(a) and FIG. 4(b), at week 12, the protein contents of phospho-AMPK protein were lower in the HF group than in the CON group in both liver and skeletal muscle ($P<0.01$ and $P<0.001$, respectively). After treatment, the protein contents of hepatic phospho-AMPK were increased in the T1, T2, and Rosi-treated groups compared with the HF group ($P<0.001$, $P<0.001$, and $P<0.01$, respectively). Upon T1, T2, and Rosi treatment, the muscular protein contents of phospho-AMPK were increased in the T1, T2, and Rosi-treated groups compared with the HF group ($P<0.001$, $P<0.001$, and $P<0.001$, respectively).

Also as shown in FIG. 4(a) and FIG. 4(b), at week 12, the proein contents of phospho-Akt/total-Akt were lower than the CON group in liver tissue ($P<0.01$). After 4 weeks of treatment of T and T2, the phospho-Akt/total-Akt protein content in liver tissue in T1- and T2-treated groups as compared with HF group ($P<0.001$ and $P<0.001$, respectively). These results indicated that treatment of the caffeamide derivatives of the present invention can increase the phosphorylation of AMPK both in skeletal muscle and liver tissue which leads to improvement of lipid metabolism. Moreover, as lipoprotein lipase is known to catalyze the transformation of triglyceride to fatty acid in blood, the reduced expression of the apo C-III gene, an inhibitor of lipoprotein lipase, by treatment of the caffeamide derivatives of the present invention as set forth above results in decrease of triglyceride concentration in blood.

In conclusion, following treatment of high-fat diet-fed mice with the caffeamide derivatives of the present invention, body weight gain and absolute tissue weight of, for instance, EWAT, visceral fat, and BAT, as well as circulating triglycerides and free fatty acids are lowered to statistically significant levels. Treating with the caffeamide derivatives of the present invention also significantly decreases the leptin concentration and increases the adiponectin level in blood. Furthermore, the cafeamide derivatives of the present invention reduce the size of both adipocyte in various different types of adipose tissues and decrease the degree of ballooning degeneration in liver tissue. Meanwhile, upon treatment with the caffeamide derivatives of the present invention, phosphorylation of AMPK in both liver and skeletal muscle is increased, while Akt phosphorylation in liver is also significantly enhanced. Therefore, the caffeamide derivatives of the present invention increases hepatic phosphorylation of AMPK while suppressing lipogenic enzyme expression (including FAS, which is a key enzyme in fatty acid synthesis), resulting in the lowering of circulating triglycerides, which is, proven beneficial for hyper-triglyceridemia or hyperlipidemia.

Hence, caffeamide derivatives of the present invention, the compound of Formula I, can be used for treatment or prevention of hyperlipidemia as pharmaceutical alternatives or supplements. For example, the pharmaceutical composition having the compound of Formula I according to the present invention can utilize an effective amount of caffeamide derivatives of the present invention to treat and improve symptoms associated with hyperlipidemia or related metabolic disorders. The composition can further comprise a pharmaceutically acceptable carrier, excipient, diluent, adjuvant, medium, or any combinations thereof. In addition, the caffeamide derivatives of the present invention can also be used in, for example and not limited to, food composition, for improving symptoms associated with hyperlipidemia; such food composition can further comprise an additive, which can be a healthy food ingredient, a food ingredient or a combination thereof. The above healthy food ingredient includes but not limit to citric acid, taurine, vitamin, pantothenic acid, nicotinic acid, or any other substances that are good for the human body; the above food ingredient includes but not limit to vegetable or meat.

The method of treating or preventing hyperlipidemia and the pharmaceutical composition performing the same provided in present invention is applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:

1. A method of treating or preventing hyperlipidemia in a subject in need thereof, comprising administrating to the subject a therapeutically effective amount of a compound of Formula I:

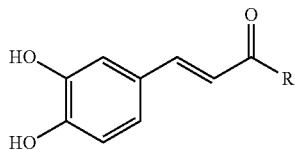

Formula I wherein R is selected from the group consisting of

n=4 or 5, NHC$_8$H$_{17}$, NH(CH$_2$)$_2$-m-Ph-F and NH(CH$_2$)$_2$OH.

2. The method of claim 1, wherein the compound of Foiinula I suppresses high-fat diet-induced increase of triglyceride concentration in blood.

3. The method of claim 1, wherein the compound of Formula I suppresses high-fat diet-induced increase of free fatty acid concentration in blood.

4. The method of claim 1, wherein the compound of Formula I decreases a hypertrophy of an adipocyte and a hepatocellular ballooning phenomenon.

5. The method of claim 4, wherein the adipocyte is from epididymal white adipose tissue (EWAT), mesenteric white adipose tissue (MWAT), retroperioneal white adipose tissue (RWAT), or visceral fat.

6. The method of claim 1, wherein the compound of Formula I reduces high-fat diet-induced increase of a body weight gain.

7. The method of claim 1, wherein the compound of Formula I increases the contents of phosphorylation of phospho-5' adenosine monophosphate-activated protein kinase (phospho-AMPK) in muscle and liver.

8. The method of claim 7, wherein the muscle is a skeletal muscle.

9. The method of claim 1, wherein the compound of Formula I decreases a level of leptin in blood.

10. The method of claim 1, wherein the compound of Formula I increases a level of adiponectin in blood.

11. The method of claim 1, wherein the therapeutically effective amount is at least 0.01 g/kg/day.

* * * * *